(12) United States Patent
Henderson et al.

(10) Patent No.: US 11,844,320 B2
(45) Date of Patent: Dec. 19, 2023

(54) FLUID ROUTING SYSTEM FOR INDOOR GROW FACILITIES

(71) Applicant: Greenspan, LLC, Alton, IL (US)

(72) Inventors: Bruys Henderson, Denver, CO (US); John Shourd, Alton, IL (US); Wayne Hoxsie, Brighton, IL (US)

(73) Assignee: Greenspan, LLC, Alton, IL (US)

( * ) Notice: Subject to any disclaimer, the term of this patent is extended or adjusted under 35 U.S.C. 154(b) by 438 days.

(21) Appl. No.: 17/210,210

(22) Filed: Mar. 23, 2021

(65) Prior Publication Data

US 2021/0212735 A1  Jul. 15, 2021

Related U.S. Application Data

(63) Continuation of application No. 15/965,335, filed on Apr. 27, 2018, now Pat. No. 10,952,384.

(51) Int. Cl.
| | |
|---|---|
| *A01G 9/24* | (2006.01) |
| *A01G 31/04* | (2006.01) |
| *A01G 7/02* | (2006.01) |
| *F16L 3/02* | (2006.01) |
| *F16L 3/22* | (2006.01) |
| *A01G 9/18* | (2006.01) |
| *A61B 90/00* | (2016.01) |

(52) U.S. Cl.
CPC ............ *A01G 9/247* (2013.01); *A01G 7/02* (2013.01); *A01G 9/18* (2013.01); *A01G 9/246* (2013.01); *F16L 3/02* (2013.01); *F16L 3/22* (2013.01); *A61B 2090/037* (2016.02)

(58) Field of Classification Search
CPC ...... A01G 31/042; A01G 31/04; A01G 9/246; A01G 9/18; A01G 9/247
See application file for complete search history.

(56) References Cited

U.S. PATENT DOCUMENTS

| | | | |
|---|---|---|---|
| 3,276,163 A | * | 10/1966 | Oepen .................. A01G 31/042 47/65 |
| 3,603,034 A | | 9/1971 | Maxwell-Stewart |
| 4,059,922 A | | 11/1977 | DiGiacinto |
| 4,218,847 A | | 8/1980 | Leroux |
| 4,704,818 A | | 11/1987 | Cameron |
| 4,965,962 A | | 10/1990 | Akagi |
| 6,061,957 A | | 5/2000 | Takashima |
| 6,216,390 B1 | | 4/2001 | Peregrin Gonzalez |
| 6,951,076 B2 | | 10/2005 | Winsbury |
| 8,984,807 B2 | | 3/2015 | Hansen et al. |
| 9,510,524 B2 | | 12/2016 | Anderson et al. |
| 2005/0102921 A1 | | 5/2005 | Mischo |
| 2009/0260284 A1 | | 10/2009 | Barbalho |
| 2010/0325975 A1 | | 12/2010 | Mischo |
| 2011/0225883 A1 | | 9/2011 | Clifford |

(Continued)

FOREIGN PATENT DOCUMENTS

| | | |
|---|---|---|
| GB | 2450142 A | 12/2008 |
| WO | 2011067575 A1 | 9/2011 |

*Primary Examiner* — Monica L Perry
(74) *Attorney, Agent, or Firm* — Armstrong Teasdale LLP

(57) ABSTRACT

A fluid routing system for use in an indoor grow facility includes a plurality of supply lines, and a plurality of frames aligned in series and spaced apart from each other. Each of the frames includes a plurality of support openings. Each of the support openings is sized to receive and retain a corresponding one of the supply lines.

20 Claims, 6 Drawing Sheets

(56) References Cited

U.S. PATENT DOCUMENTS

| | | | |
|---|---|---|---|
| 2015/0250115 A1* | 9/2015 | Pickell | A01G 31/042 47/62 R |
| 2018/0359953 A1* | 12/2018 | Millar | A01G 31/06 |
| 2018/0359954 A1* | 12/2018 | Millar | A01G 9/247 |
| 2018/0359956 A1* | 12/2018 | Millar | A01G 31/042 |
| 2018/0359965 A1* | 12/2018 | Millar | A01G 7/045 |
| 2018/0359971 A1* | 12/2018 | Millar | A01G 31/042 |
| 2020/0100445 A1* | 4/2020 | Saba | G06F 7/00 |
| 2020/0236879 A1* | 7/2020 | Millar | A01G 27/008 |

* cited by examiner

FLUID ROUTING SYSTEM FOR INDOOR GROW FACILITIES

CROSS REFERENCE TO RELATED APPLICATIONS

This application is a continuation of, and claims priority to, U.S. patent application Ser. No. 15/965,335, filed Apr. 27, 2018, the entire contents of which are hereby incorporated by reference in their entirety.

BACKGROUND

The field of the disclosure relates generally to indoor grow facilities and, more particularly, to systems for fluid circulation to plants in greenhouses and other indoor grow facilities.

At least some known indoor grow facilities, such as greenhouses, include air handling systems for circulating conditioned or recycled air to plants housed therein, and watering systems for circulating water, including nutrient-enriched water, to the plants. Moreover, at least some known indoor grow facilities include additional supply systems, such as carbon dioxide supply systems for routing supplemental carbon dioxide to the plants. In addition, at least some industrial greenhouses are as large as 45,000 square feet and new indoor grow facilities may continue to grow in size, resulting in a need for correspondingly lengthy supply lines routed to plants throughout the facility.

The various supply systems in at least some known indoor grow facilities are implemented separately from each other, resulting in ad hoc routing of supply lines and, often, unintended interference or entanglement among the supply lines or other components of the various systems. At least some known indoor grow facilities consequently experience inefficient use of potential grow space within the facility, difficulty in re-routing supply lines to accommodate reorganization of the grow space, and/or difficulty in re-configuring one or more of the supply systems without requiring shutdown or re-work of the other systems as well. Moreover, at least some known air handling systems for circulating conditioned or recycled air are configured for installation adjacent to a ceiling of the facility, and/or are sized to condition the air throughout an entire floor-to-ceiling space of the facility, increasing both an initial cost and a maintenance cost of the systems.

BRIEF DESCRIPTION

In one aspect, a fluid routing system for use in an indoor grow facility is provided. The routing system includes a plurality of supply lines, and a plurality of frames aligned in series and spaced apart from each other. Each of the frames includes a plurality of support openings. Each of the support openings is sized to receive and retain a corresponding one of the supply lines.

In another aspect, a fluid routing system for use in an indoor grow facility is provided. The routing system includes a plurality of frames aligned in series and spaced apart from each other. Each of the frames includes a plurality of support openings. The routing system also includes an air line retained in a first of the plurality of support openings of each of the frames, and a drip feed line retained in a second of the plurality of support openings of each of the frames.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Figure 1:
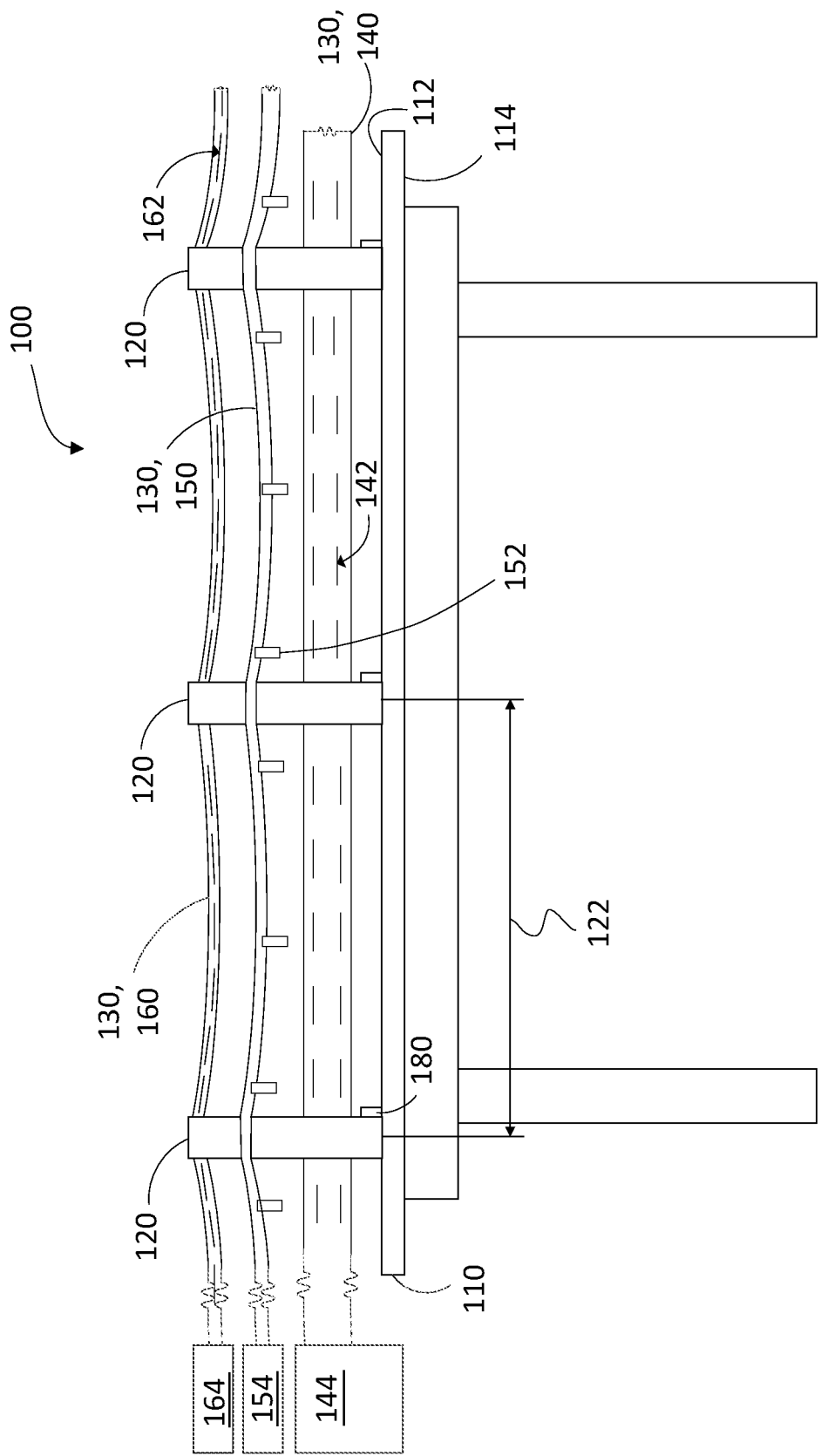
FIG. 1 is a side elevation view of an example greenhouse air and nutrient routing system.
Figure 2:
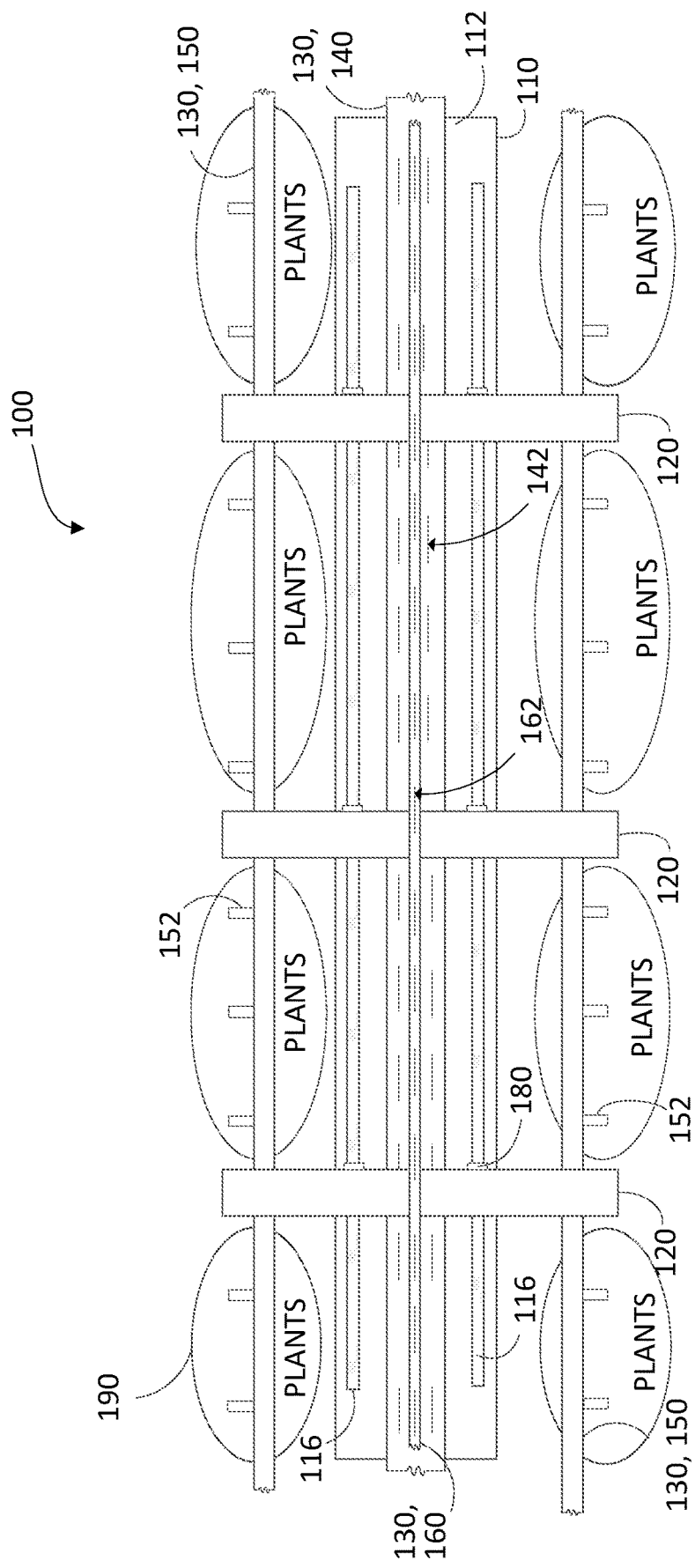
FIG. 2 is a top view of the routing system of FIG. 1 having plants positioned on opposing sides of the routing system.

FIG. 1 is a side elevation view of an example fluid routing system 100 (hereinafter referred to as the "routing system") for use in an indoor grow facility, such as a greenhouse. FIG. 2 is a top view of the routing system 100 having plants 190 positioned on opposing sides of the routing system 100. The routing system includes a plurality of frames 120 aligned in series and spaced apart from each other by a longitudinal distance 122. The frames 120 cooperate to support a plurality of supply lines 130. In the illustrated embodiment, each adjacent pair of frames 120 is spaced apart by a substantially equal longitudinal distance 122. In alternative embodiments, the longitudinal distance 122 varies between at least some pairs of adjacent frames 120. For example, but not by way of limitation, the longitudinal distance 122 is between three and eight feet. In some embodiments, the supply lines 130 are between about 50 feet and about 150 feet in length, and the plurality of frames 120 are spaced in series along the length of the supply lines 130 at the longitudinal distance 122 of about 5 feet. Although only three frames 120 are shown arranged longitudinally in FIG. 1, it should be understood that any suitable number of frames 120 is arranged longitudinally to accommodate a longitudinal length of the row of plants 190. Moreover, although the frames 120 are shown aligned along a straight line in FIG. 1, it should be understood that the frames 120 may be aligned in series along any suitable curvilinear path of the supply lines 130.

In the illustrated embodiment, each frame 120 is substantially identical to the other frames 120, such that each frame 120 is interchangeably usable during installation, repair, and/or reconfiguration of the routing system 100. In alternative embodiments, at least one frame 120 is other than substantially identical to others of frames 120. Each frame 120 includes a plurality of support openings 310 (shown in FIGS. 3 and 5) each sized to receive and retain a corresponding supply line 130.

In the illustrated embodiment, the routing system 100 includes at least three supply lines 130. More specifically, a first supply line 130, designated as air line 140, is fluidly coupled to an air source 144. In some embodiments, the air source 144 is an HVAC system that conditions at least one of a temperature and a humidity of the air supplied to air line 140. In other embodiments, the air source 144 is a fan, for example, that supplies air recycled from another location within or outside the indoor grow facility.

In the illustrated embodiment, the air line 140 includes a plurality of apertures 142 configured to supply air from within air line 140 to plants 190 adjacent to the routing system 100. For example, but not by way of limitation, the apertures 142 are slots formed through a sidewall of the air line 140. In the illustrated embodiment, the apertures 142 are distributed longitudinally along the air line 140 and on opposing lateral sides of the air line 140 to provide a steady supply of air to plants 190 on either side of the routing system 100 along a length of the routing system 100. In alternative embodiments, the apertures 142 are formed and arranged in any suitable fashion that enables the air line 140 to function as described herein.

In the illustrated embodiment, a second supply line 130, designated as drip feed line 150, is fluidly coupled to a liquid plant feed source 154. For example, but not by way of limitation, the liquid plant feed includes water enriched with suitable nutrients tailored to improve the grow of the plants 190 positioned adjacent to the routing system 100. More specifically, in the illustrated embodiment, the second supply line 130 includes a pair of drip feed lines 150 extending in parallel on opposing lateral sides of frames 120. In alternative embodiments, the second supply line 130 includes any suitable number of drip feed lines 150.

Each drip feed line 150 includes a plurality of drip feed outlets 152 configured to supply liquid plant feed from within the respective drip feed line 150 to plants 190 adjacent to the corresponding lateral sides of the routing system 100. For example, but not by way of limitation, the outlets 152 are nozzles coupled to a sidewall of drip feed line 152 and oriented to direct liquid plant feed from within the drip feed line 150 towards the bases of the plants 190 adjacent to the routing system 100. In the illustrated embodiment, the outlets 152 are distributed longitudinally along each drip feed line 150 and oriented downward and partially laterally outward from the frames 120 to provide a steady supply of liquid plant feed to the plants 190 along a length of the routing system 100. In alternative embodiments, the outlets 152 are formed and arranged in any suitable fashion that enables the drip feed line 150 to function as described herein.

In the illustrated embodiment, a third supply line 130, designated as carbon dioxide line 160, is fluidly coupled to a carbon dioxide source 164. In the illustrated embodiment, the carbon dioxide line 160 includes a plurality of apertures 162 configured to supply carbon dioxide from within carbon dioxide line 160 to plants 190 adjacent to the routing system 100. For example, but not by way of limitation, the apertures 162 are slots formed through a sidewall of the carbon dioxide line 160. In the illustrated embodiment, the apertures 162 are distributed longitudinally along the carbon dioxide line 160 and on opposing lateral sides of the carbon dioxide line 160 to provide a steady supply of carbon dioxide to the plants 190 on either side of the routing system 100 along the length of the routing system 100. In alternative embodiments, the apertures 162 are formed and arranged in any suitable fashion that enables the carbon dioxide line 160 to function as described herein. In certain embodiments, the use of a separate carbon dioxide line 160, rather than for example adjusting carbon dioxide content within air line 140, facilitates improved tuning of an amount of carbon dioxide delivered to the plants 190.

In other embodiments, the routing system 100 includes any suitable number of additional or alternative supply lines 130 as is suitable for plants 190.

In the illustrated embodiment, the routing system 100 further includes a support surface 110 configured to support the frames 120 in relation to the plants 190. For example, but not by way of limitation, the support surface 100 is a table sized to position the drip feed outlets 152 along the sides of the routing system 100 directly above the bases of the respective rows of plants 190 on opposing sides of the routing system 100, and/or to position air and carbon dioxide apertures 142, 162 directly adjacent to the leaves of the plants 190. In alternative embodiments, the support surface 110 is any suitable support surface that enables the routing system 100 to function as described herein.

In the illustrated embodiment, the routing system 100 further includes a plurality of connectors 180 configured to secure the frames 120 to the support surface 110. For example, the support surface 110 defines a top face 112, an opposite bottom face 114, and at least one slot 116 that extends through the support surface 110 from the top face 112 to the bottom face 114. More specifically, in the illustrated embodiment, the support surface 110 defines two slots 116 adjacent to opposing lateral sides of the support surface 110. Alternatively, the support surface 110 defines more or fewer than two slots 116. The connectors 180 extend through the slots 116 and through a horizontally oriented flange 370 (shown in FIGS. 3 and 5) of the frames 120 to secure the frames 120 to the support surface 110. Moreover, in some embodiments, the connectors 180 are loosened to facilitate sliding the frames 120 and connectors 180 along the slots 116 to a desired longitudinal position along the support surface 110, and then tightened to re-secure the frames to the support surface. In certain embodiments, the connectors 180 are spring-loaded to facilitate transitioning between such a sliding adjustment mode and a secured condition. In alternative embodiments, the connectors 180 are configured to secure the frames 120 to the support surface 110 in any suitable fashion that enables the routing system 100 to function as described herein. In other alternative embodiments, the routing system 100 does not include the connectors 180.

Figure 3:
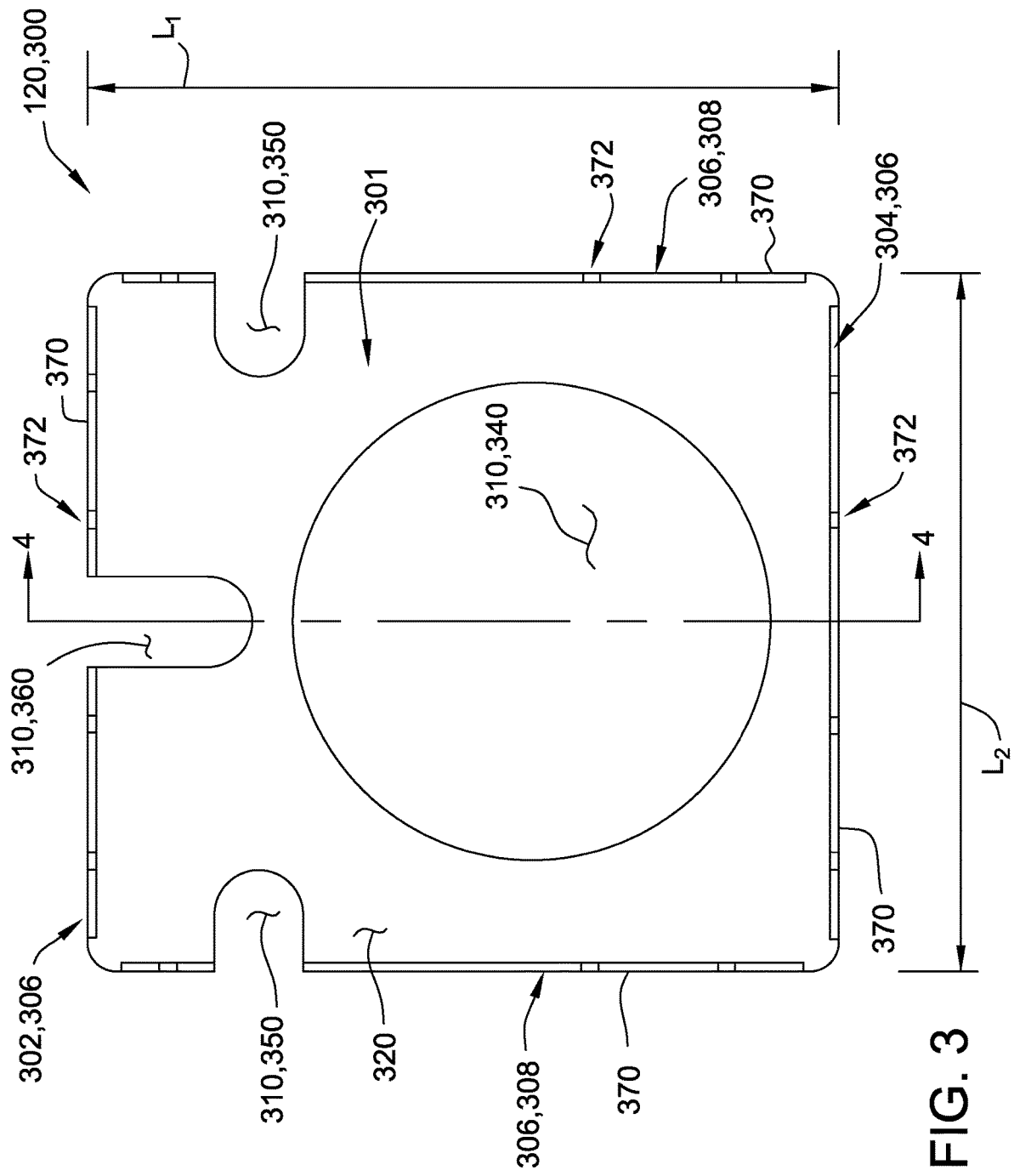
FIG. 3 is a front view of an example routing system frame.
Figure 4:
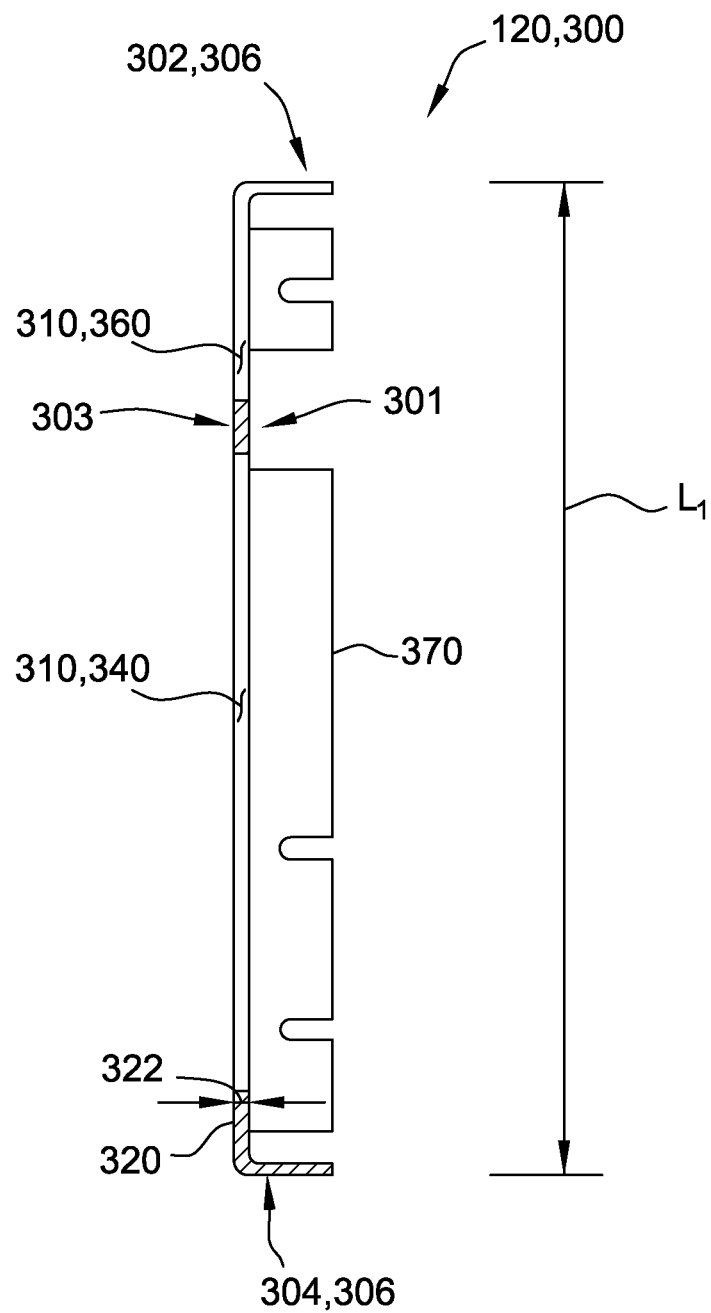
FIG. 4 is a sectional view of the routing system frame taken along line "4-4" in FIG. 3.

FIG. 3 is a front view of an example routing system frame 120, designated as frame 300, suitable for use with the routing system 100 shown in FIGS. 1 and 2. FIG. 4 is a sectional view of the frame 300 taken along line 4-4 in FIG. 3. The frame 300 includes a plate portion 320 that extends from a first face 301 to an opposite second face 303. The first and second faces 301, 303 are bounded by a plurality of edges 306. The plate portion 320 also defines a plurality of support openings 310 each extending longitudinally therethrough from the first face 301 to the second face 303. Each support opening 310 is sized to receive and retain a corresponding supply line 130 (shown in FIGS. 1 and 2). Because the support openings 310 are defined through the plate portion 320, the supply lines 130 are retained generally within a profile defined by the edges 306 of the plate portion 320, rather than being supported by additional arms or struts that project outward from the frame 300. In some embodiments, the frame 300 thus reduces a footprint of the routing system 100 and thereby increases a usable grow space in the facility. Additionally or alternatively, the frame 300 thus decreases a safety risk posed by inadvertent contact of personnel or other equipment with such projections. Additionally or alternatively, the absence of such additional arms or struts improves an ease of shipping, storage, and handling of the frames 300 and assembly of the routing system 100.

In certain embodiments, the plate portion 320 has a thickness 322 defined between the first face 301 and the second face 303 of less than about 0.25 inches. For example, in the illustrated embodiment, the thickness 322 is about 0.150 inches. In some embodiments, the relatively small thickness 322 of the plate portion 320 of frames 300 facilitates reducing a manufacturing cost of the frames 300. Additionally or alternatively, the relatively small thickness 322 of the plate portion 320 facilitates reducing a weight and, thus, increasing an ease of handling the frames 300 during installation of the routing system 100 In alternative embodiments, the plate portion 320 has any suitable thickness 322 that enables the frame 300 to function as described herein.

In the illustrated embodiment, the plate portion 320 has a generally rectangular shape. More specifically, the plate portion 320 extends vertically from a base edge 304 to a top edge 302 over a height L1, and extends laterally between a pair of lateral edges 308 over a base width L2. In alternative embodiments, the plate portion 320 has any suitable shape that enables the frame 300 to function as described herein. In some embodiments, height L1 and base width L2 are each at least about 14 inches, providing sufficient stability to the frame 300 while accommodating a size of the support openings 310 that corresponds to a size of the supply lines 130 necessary to provide a sufficient flow rate of fluids to the plants 190. In a particular embodiment, the supply lines 130 are between about 50 feet and about 150 feet in length, and the frames 300 are spaced about 5 feet apart along the length of the supply lines 130 and have height L1 and base width L2 each being about 18 inches. In alternative embodiments, height L1 and base width L2 each have any suitable value that enables the frames 300 to function as described herein. It should be understood that height L1 and base width L2 need not be equal to each other.

With reference to FIGS. 1-4, a first of the plurality of support openings 310, designated air support opening 340, is sized to receive the air line 140 therethrough in a clearance fit. In the illustrated embodiment, the air support opening 340 extends generally through a mid-portion of the plate portion 320, such that the air support opening 340 is circumferentially closed. Thus, the air support opening 340 positions the air line 140 generally midway between the two rows of plants 190 on opposing lateral sides of the routing system 100, providing an even flow of air to both rows. In alternative embodiments, the air support opening 340 is positioned with respect to the plate portion 320 in any suitable fashion that enables the routing system 100 to function as described herein.

In the illustrated embodiment, the air line support opening 340 is circular to accommodate the air line 140 having a corresponding circular cross-section. In alternative embodiments, the shape of the air support opening 340 corresponds to any suitable shape of the air line 140. In some embodiments, the diameter of the air line 140, and thus of the air support opening 340, is selected based on the longitudinal length of the row of plants 190 to provide a suitable flow of air to the entire length of the row. For example, but not by way of limitation, the air support opening 340 has a diameter of at least about 7 inches to accommodate a row of plants 190 in a typical indoor grow facility.

In certain embodiments, a ratio of a diameter of the air support opening 340 to the base width L2 of the plate portion 320 is less than about 0.80, for example to facilitate stability of the frame 120. For example, in the illustrated embodiment, the ratio of the diameter of the air support opening 340 to the base width L2 of the plate portion 320 is about 0.68.

In alternative embodiments, the ratio of the diameter of the air support opening 340 to the base width L2 of the plate portion 320 is any suitable value that enables the routing system 100 to function as described herein.

In the illustrated embodiment, a second of the plurality of support openings 310, designated drip feed support opening 350, is sized to receive the drip feed line 150 therethrough in a clearance fit. More specifically, in the illustrated embodiment, the second support opening 310 includes a pair of drip feed support openings 350 on opposing lateral sides of frame 300 to receive the corresponding pair of drip feed lines 150. In alternative embodiments, the second supply line 130 includes any suitable number of drip feed support openings 350.

In the illustrated embodiment, each drip feed support opening 350 opens to a respective lateral edge 308 of the plate portion 320, such that the drip feed support opening 350 is circumferentially open. Thus, the drip feed support opening 350 enables easy removal and replacement of the drip feed lines 150 from the routing system 100. For example, a number of the drip feed outlets 152 become clogged after extended usage. The drip feed lines 150 are simply changed out, thus avoiding a need to take the routing system 100 out of service to cleanse and rinse the original drip feed lines 150 in situ. For another example, after the routing system 100 is used with a first type of plant 190, a different type of plant 190 with incompatible drip feed nutrient requirements is to be nourished by the routing system 100. The drip feed lines 150 are simply changed out, thus avoiding a need to cleanse and rinse the original drip feed lines 150 prior to accommodating the different type of plant 190. In alternative embodiments, each drip feed support opening 350 is positioned with respect to the plate portion 320 in any suitable fashion that enables the routing system 100 to function as described herein.

In the illustrated embodiment, a third of the plurality of support openings 310, designated carbon dioxide support opening 360, is sized to receive the carbon dioxide feed line 160 therethrough in a clearance fit. In the illustrated embodiment, the carbon dioxide support opening 360 opens to the top edge 302 of the plate portion 320, such that the carbon dioxide support opening 360 is circumferentially open, facilitating easy removal and replacement of the carbon dioxide feed line 160 from the routing system 100, similar to as described above for drip feed lines 150. More specifically, the carbon dioxide support opening 360 is positioned generally midway along the top edge 302, and thus generally midway between the two rows of plants 190 on opposing lateral sides of the routing system 100, providing an even flow of carbon dioxide to both rows. In alternative embodiments, the carbon dioxide support opening 360 is positioned with respect to the plate portion 320 in any suitable fashion that enables the routing system 100 to function as described herein.

In the illustrated embodiment, the frame 300 also includes a flange 370 extending from at least portions of the edges 306 of the plate portion 320. In some embodiments, the flange 370 facilitates an increased structural stability of frame 300 in supporting the plurality of supply lines 130. In the illustrated embodiment, the flange 370 is oriented generally perpendicular to the plate portion 320. In alternative embodiments, the flange 370 is oriented in any suitable fashion that enables the frame 300 to function as described herein. In alternative embodiments, the frame 300 does not include the flange 370.

In the illustrated embodiment, the flange 370 does not traverse the support openings 310 that extend to the edges 306 of the plate portion 320, maintaining the ease of insertion and removal of the corresponding supply lines 130 as described above. In alternative embodiments, the flange 370 traverses at least one of the support openings 310 that extend to the edges 306.

In the illustrated embodiment, the flange 370 includes a plurality of flange openings 372 defined therein and extending therethrough. In some embodiments, flange openings 372 facilitate securing frame 300 to other support structures in the indoor grow facility, such as by accommodating connectors. For example, flange openings 372 in flange 370 extending from base edge 304 are sized to receive connectors 180. In alternative embodiments, the flange 370 does not include flange openings 372.

In some embodiments, the frame 300 is formed from a metal material, such as but not limited to aluminum. Moreover, in some such embodiments, the frame 300 is unitarily formed from a single piece of sheet metal that is pressed and punched to form the plate portion 320, the flange 370, and the support openings 310. In certain embodiments, unitary formation of the frame 300 from a single sheet of material decreases a manufacturing cost and improves a structural integrity of the frame 300. In alternative embodiments, the frame 300 is formed from separate pieces of metal coupled together, such as by welding.

Alternatively, in some embodiments, the frame 300 is formed from a suitable plastic material, such as via injection molding.

In other alternative embodiments, the frame 300 is formed via an additive layer manufacturing process (e.g., 3-D printing). For example, a computer aided design (CAD) model of the frame 300 is sliced into a series of thin, parallel layers, such that a corresponding distribution of material within each sequential layer of the frame 300 is defined. A computer numerically controlled (CNC) machine deposits successive layers of material in accordance with the slices of the CAD model and fuses the successive layers together to form the frame 300. The material is, for example, powdered metal forming a metallic frame 300 or plastic forming a plastic frame 300. Alternatively, any suitable additive manufacturing process and material is used.

Figure 5:
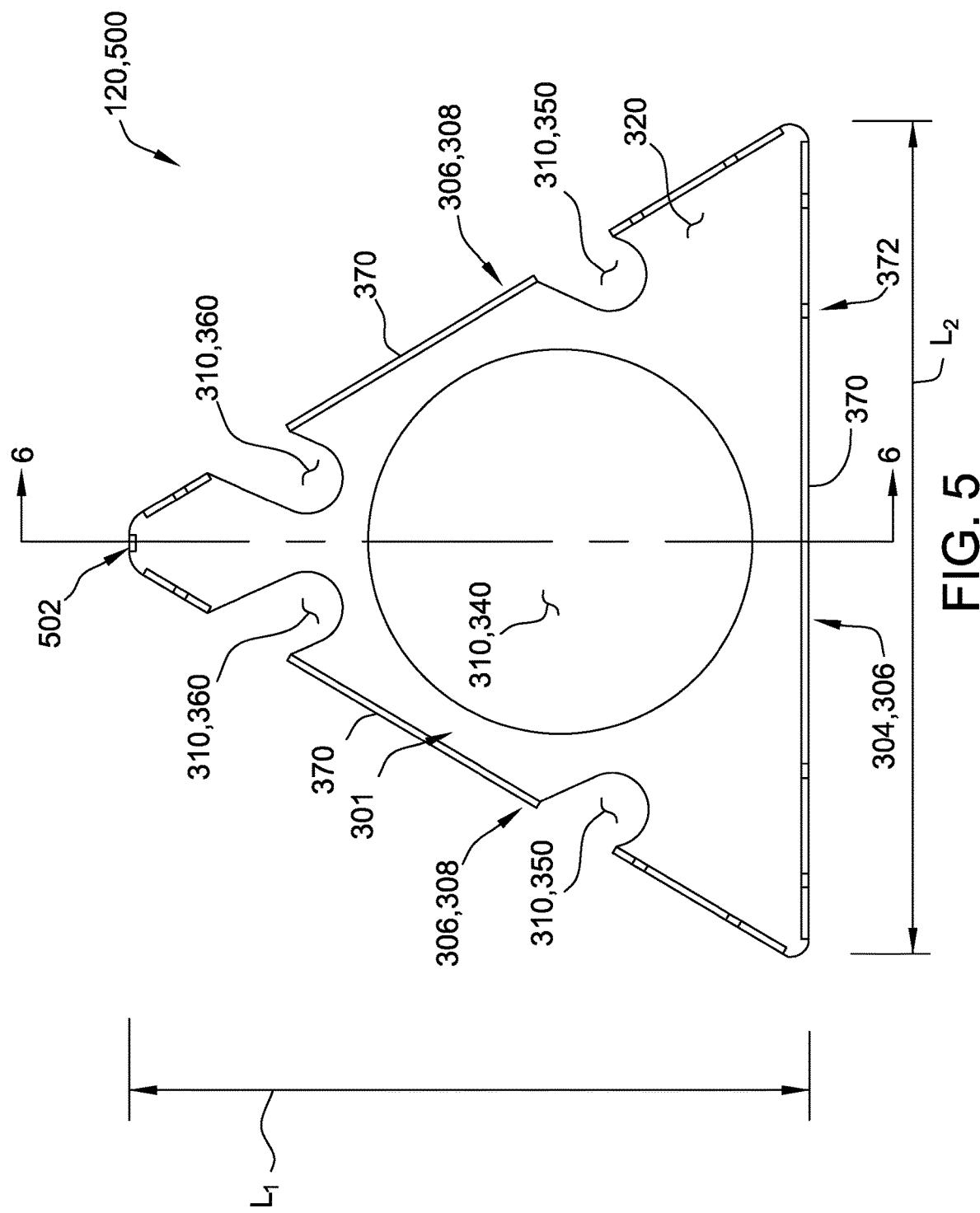
FIG. 5 is a front view of another example routing system frame.
Figure 6:
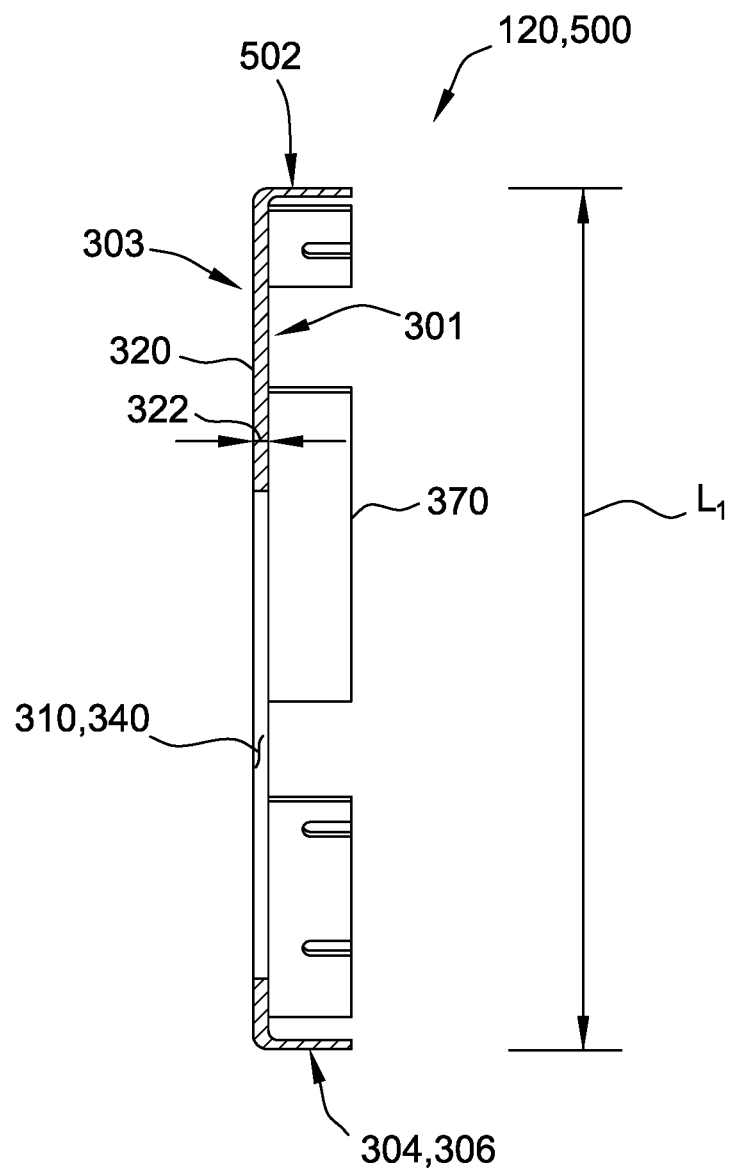
FIG. 6 is a sectional view of the routing system frame of FIG. 5, taken along line "6-6" in FIG. 5.

FIG. 5 is a front view of another example routing system frame 120, designated as frame 500, suitable for use with the routing system 100 shown in FIGS. 1 and 2. FIG. 6 is a sectional view of the frame 500 taken along line 6-6 in FIG. 5. The frame 500 is substantially identical to the frame 300 except as otherwise described. In particular, the plate portion 320 of the frame 500 has a generally triangular shape. More specifically, the plate portion 320 extends vertically from the base edge 304 to a top vertex 502 over the height L1, and extends laterally between the pair of lateral edges 308 that taper from a base width L2 at the base edge 304 towards a zero width at the vertex 502. In some embodiments, the triangular shape of the plate portion 320 results in relatively less material needed to make the frame 500, as well as a lower center of gravity of the frame 500 and, thus, an increased stability of the frame 500 against tipping. In alternative embodiments, the plate portion 320 has any suitable shape that enables the frame 500 to function as described herein.

In some embodiments, height L1 and base width L2 are each at least about 14 inches, providing sufficient stability to the frame 500 while accommodating a size of the support openings 310 that corresponds to a size of the supply lines 130 necessary to provide a sufficient flow rate of fluids to the plants 190. In a particular embodiment, the supply lines 130 are between about 50 feet and about 150 feet in length, and the frames 500 are spaced about 5 feet apart along the length of the supply lines 130 and have height L1 of about 14.5 inches and base width L2 of about 18 inches. In alternative embodiments, height L1 and base width L2 each have any suitable value that enables the frames 500 to function as described herein.

Also in contrast to the frame 300, the plate portion 320 of the frame 500 defines a pair of carbon dioxide support openings 360 that open to the respective lateral edges 308. Thus, the frame 500 supports the use of a pair of carbon dioxide supply lines 160 in the routing system 100, rather than a single carbon dioxide supply line.

The frame 500 is formed in substantially identical fashion as that described above for the frame 300.

The above-described embodiments of fluid routing systems for use in indoor grow facilities overcome at least some disadvantages of known systems. In particular, the above-described embodiments consolidate circulation of conditioned or recycled air, nutrient drip feed, and/or carbon dioxide along a single path using a consistent framework formed from interchangeable frame components. Consolidating these supply systems reduces their footprint and increases usable growing space. As one example, with the supply lines consolidated and off of the floor, plants stationed on rolling tables can be successively rolled into position adjacent to the stationary routing system to cycle a large number of plants through nutrient sessions. Additionally, providing the carried fluids, including air, directly to plants and plant bases improves plant health while reducing or eliminating a need for costly overhead air handling/ circulation apparatus, and reducing required air handling tonnage. The embodiments therefore add efficiency and space to indoor grow facilities, reduce costs associated with operation, and facilitate healthier plant growth.

Example embodiments of greenhouse air and nutrient routing systems are described above in detail. The greenhouse air and nutrient routing systems are not limited to the specific embodiments described herein, but rather, components of the greenhouse air and nutrient routing systems may be used independently and separately from other components described herein. For example, the routing system frames described herein may be used with a variety of plant growth operations, including and without limitation, large scale and small scale outdoor plant growing operations, public and private gardens, and other grow facilities. Embodiments disclosed enable efficient distribution of fluid nutrients to plants without requiring significant modifications to other components of a greenhouse or other plant growth operation. Thus, the disclosed volutes may be readily incorporated into existing greenhouse or other plant growth operation designs.

As used herein, the terms "about," "substantially," "essentially" and "approximately" when used in conjunction with ranges of dimensions, concentrations, temperatures or other physical or chemical properties or characteristics is meant to cover variations that may exist in the upper and/or lower limits of the ranges of the properties or characteristics, including, for example, variations resulting from rounding, measurement methodology or other statistical variation. Additionally, unless otherwise indicated, the terms "first," "second," etc. are used herein merely as labels, and are not intended to impose ordinal, positional, or hierarchical requirements on the items to which these terms refer. Moreover, reference to, for example, a "second" item does not require or preclude the existence of, for example, a "first" or lower-numbered item or a "third" or higher-numbered item.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing[s] shall be interpreted as illustrative and not in a limiting sense.

What is claimed is:

1. A method of providing nutrient feedings to plants in an indoor grow facility, said method comprising:
arranging a plurality of frames in series on a support surface, wherein each of the frames includes a plurality of support openings, and wherein a plurality of supply lines are supported by the support openings of the frames, each of the supply lines including supply openings distributed longitudinally therealong;
cycling groups of plants through a feeding position adjacent to the arranged frames while the arranged frames are substantially stationary; and
flowing nutrients into the supply lines and through the supply openings to each group of plants while the respective group is in the feeding position.

2. The method in accordance with claim 1, wherein said arranging the frames comprises independently positioning each frame along the support surface with respect to the frames adjacent in series thereto.

3. The method in accordance with claim 1, further comprising:
replacing, while the arranged frames are substantially stationary, an initial supply line of the plurality of supply lines with a different supply line to define a second plurality of supply lines supported by the support openings of the frames; and
flowing the nutrients through the second plurality of supply lines to an additional group of plants.

4. The method in accordance with claim 3, wherein said replacing the initial supply line is performed in response to detecting a clog in the initial supply line.

5. The method in accordance with claim 3, wherein the additional group of plants has different nutrient requirements as compared to the plurality of groups of plants, and wherein said replacing the initial supply line is performed in response to the different nutrient requirements.

6. The method in accordance with claim 1, further comprising routing an air line of the plurality of supply lines through an air support opening of the frames.

7. The method in accordance with claim 6, wherein each of the frames includes a plate portion, said routing the air line further comprises routing the air line through the air support opening defined in a mid-portion of the plate portion, wherein the air support opening is circumferentially closed.

8. The method in accordance with claim 6, wherein the supply openings of the air line are further distributed on opposing lateral sides of the air supply line, and wherein the feeding position includes at least two feeding positions on opposing sides of the arranged frames.

9. The method in accordance with claim 1, further comprising routing a drip feed line of the plurality of supply lines through a drip feed support opening of the frames.

10. The method in accordance with claim 9, wherein each of the frames includes a plate portion, said routing the drip feed line further comprises routing the drip feed line through the drip feed support opening that opens to an edge of the plate portion, such that the drip feed support opening is circumferentially open.

11. The method in accordance with claim 10, wherein said routing the drip feed line comprises routing a pair of drip feed lines through a corresponding pair of drip feed support openings that open to opposing lateral edges of the plate portion, and wherein the feeding position includes at least two feeding positions on corresponding opposing sides of the arranged frames.

12. The method in accordance with claim 1, further comprising routing a carbon dioxide line of the plurality of supply lines through a carbon dioxide support opening of the frames.

13. The method in accordance with claim 12, wherein each of the frames includes a plate portion, said routing the carbon dioxide line further comprises routing the carbon dioxide line through the carbon dioxide support opening that opens to an edge of the plate portion, such that the carbon dioxide support opening is circumferentially open.

14. The method in accordance with claim 13, wherein said routing the carbon dioxide line comprises routing a pair of carbon dioxide lines through a corresponding pair of carbon dioxide support openings that open to opposing lateral edges of the plate portion, and wherein the feeding position includes at least two feeding positions on corresponding opposing sides of the arranged frames.

15. The method in accordance with claim 12, wherein the supply openings of the carbon dioxide line are further distributed on opposing lateral sides of the carbon dioxide line, and wherein the feeding position includes at least two feeding positions on opposing sides of the arranged frames.

16. The method in accordance with claim 1, wherein each of the frames includes a plate portion, said method further comprising routing the plurality of supply lines through the plate portion of each frame such that the supply lines are retained generally within a profile defined by edges of the plate portion.

17. The method in accordance with claim 1, wherein said arranging the plurality of frames on the support surface comprises arranging the plurality of frames on a table.

18. The method in accordance with claim 1, wherein said cycling the groups of plants through the feeding position comprises:
positioning each group of plants on a rollable surface; and
after said positioning, successively rolling each of the rollable surfaces into the feeding position.

19. The method in accordance with claim 1, wherein said arranging the frames comprises arranging the frames in a straight line.

20. The method in accordance with claim 1, wherein said arranging the frames comprises arranging the frames at least partially along a curved path.

* * * * *